(12) United States Patent
Seesselberg et al.

(10) Patent No.: US 10,159,406 B2
(45) Date of Patent: Dec. 25, 2018

(54) OPHTHALMIC SURGICAL APPARATUS FOR INSERTING INTRAOCULAR LENSES IN EYES

(71) Applicant: Carl Zeiss Meditec AG, Jena (DE)

(72) Inventors: Markus Seesselberg, Aalen (DE); Marco Wilzbach, Stuttgart (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 15/432,754

(22) Filed: Feb. 14, 2017

(65) Prior Publication Data

US 2017/0156583 A1 Jun. 8, 2017

Related U.S. Application Data

(63) Continuation of application No. PCT/EP2015/068771, filed on Aug. 14, 2015.

(30) Foreign Application Priority Data

Aug. 14, 2014 (DE) .................. 10 2014 111 630

(51) Int. Cl.
*A61B 3/00* (2006.01)
*A61B 3/10* (2006.01)
(Continued)

(52) U.S. Cl.
CPC .......... *A61B 3/0025* (2013.01); *A61B 3/0033* (2013.01); *A61B 3/102* (2013.01);
(Continued)

(58) Field of Classification Search
CPC .......... A61B 3/14; A61B 3/0025; A61B 3/12; A61B 3/102; A61B 3/0058
(Continued)

(56) References Cited

U.S. PATENT DOCUMENTS 7,556,378 B1 7/2009 Ianchulev
9,526,410 B2 * 12/2016 Hauger ............... A61F 9/00736
(Continued)

OTHER PUBLICATIONS

Office action and English translation of the Office action of the German Patent Office dated Jun. 11, 2015 in German patent application 10 2014 111 630.5 on which the claim of priority is based.
(Continued)

*Primary Examiner* — Mohammad Hasan
(74) *Attorney, Agent, or Firm* — Walter Ottesen, P.A.

(57) ABSTRACT

An ophthalmic surgical apparatus including: a control device; a user interface which, at least intermittently, has data communication with the control device; a first measuring device configured for determining at least one value intraoperatively, the value being characteristic for an eye to be treated by surgery; a second measuring device configured for determining at least one value preoperatively and/or intraoperatively, the value being characteristic for the eye to be treated by surgery, and including a first computing unit which is suitable and intended, using the value determined intraoperatively and the value determined preoperatively and/or intraoperatively, for ascertaining at least one first output value which is characteristic for at least one intraocular lens to be selected, wherein the user interface at least preferably includes an output device suitable for outputting the output value or a value derived therefrom.

21 Claims, 4 Drawing Sheets

(51) Int. Cl.
  *A61B 3/103* (2006.01)
  *A61B 3/107* (2006.01)
  *A61F 9/007* (2006.01)
  *A61B 34/10* (2016.01)
  *A61B 34/00* (2016.01)
  *A61B 3/13* (2006.01)
  *A61B 3/16* (2006.01)
  *A61F 2/16* (2006.01)
  *A61B 3/117* (2006.01)

(52) U.S. Cl.
  CPC ............ *A61B 3/103* (2013.01); *A61B 3/1005* (2013.01); *A61B 3/107* (2013.01); *A61B 3/13* (2013.01); *A61B 3/16* (2013.01); *A61B 34/10* (2016.02); *A61B 34/25* (2016.02); *A61F 2/1662* (2013.01); *A61F 9/00736* (2013.01); *A61B 3/117* (2013.01); *A61B 2034/104* (2016.02); *A61B 2034/108* (2016.02)

(58) Field of Classification Search
  USPC .................................................. 351/200–246
  See application file for complete search history.

(56) References Cited

U.S. PATENT DOCUMENTS

| | | | |
|---|---|---|---|
| 9,844,321 B1* | 12/2017 | Ekvall | A61B 3/13 |
| 2011/0304819 A1* | 12/2011 | Juhasz | A61B 3/102 |
| | | | 351/206 |
| 2014/0042419 A1* | 2/2014 | Okumoto | H01L 27/1292 |
| | | | 257/40 |

OTHER PUBLICATIONS

Translation of the Written Opinion of the International Searching Authority dated Oct. 16, 2015 of European patent application PCT/EP2015/068771 on which this application is based.

International Search Report of the international searching authority dated Oct. 16, 2015 in international patent application PCT/EP2015/068771 on which the claim of priority is based.

* cited by examiner

OPHTHALMIC SURGICAL APPARATUS FOR INSERTING INTRAOCULAR LENSES IN EYES

CROSS REFERENCE TO RELATED APPLICATIONS

This application is a continuation application of international patent application PCT/EP2015/068771, filed Aug. 14, 2015, designating the United States and claiming priority from German application 10 2014 111 630.5, filed Aug. 14, 2014, and the entire content of both applications is incorporated herein by reference.

FIELD OF THE INVENTION

The present invention relates to an ophthalmic surgical apparatus and to a selection method for selecting a lens and, in particular, an intraocular lens.

BACKGROUND OF THE INVENTION

The prior art has disclosed many methods and apparatuses which serve to improve eye operations and, in particular, the insertion of intraocular lenses (IOLs) into eyes. Thus, methods in which a clouded natural lens of the eye of a patient is removed by surgery and replaced by an artificial lens (in particular an intraocular lens, IOL) are known.

Likewise, procedures in which a further lens is inserted in addition to the still present natural lens of the eye in order to improve the visual acuity of the eye are also known. A large number of very different intraocular lenses are commercially available. Hence, a problem always arising in such operations is that of selecting a suitable type of intraocular lens from different types. By way of example, these available intraocular lenses differ in respect of the refractive index thereof, the employed lens material, the radii of curvature of the lens surfaces, an axial distance between the lens surfaces, the type of haptics, the diameter and further properties.

Furthermore, different types of intraocular lenses also exist, for example intraocular lenses with aspherical lens surfaces or lens surfaces which are free-form surfaces without rotational symmetry. Additionally, intraocular lenses with different zones or intraocular lenses with diffractively optical elements are also known.

To ensure that a suitable IOL is inserted into a patient, it is possible to select an IOL with appropriate refractive power in advance in the case of a patient eye in a phakic state in order thus to achieve a post-surgical target refraction desired by the patient. In this procedure, the post-surgical position, in particular, of the IOL is predicted, in particular depending on a measured capsular bag position. The predictions may be used for improved positioning and centering of the implanted IOL. Alternatively, a surgeon may be assisted in the decision as to whether the implanted lens should be replaced by an IOL fitting into the patient eye in an improved manner.

What should be noted here is that the IOL is initially implanted and the eyesight of the eye is subsequently assessed—still during the operation. In these cases, it may be necessary to replace the IOL if a desired target refraction of the patient eye after surgery cannot be achieved with the refractive power of the implanted IOL. Such a replacement of the IOL is connected with increased complexity during a cataract operation. Moreover, this may also be accompanied by medical complications. Hence, this described method is quality control to the extent of whether an already selected IOL also leads to the desired target refraction.

SUMMARY OF THE INVENTION

It is an object of the invention to provide an apparatus and, optionally, a method as well, which avoid such replacement of the IOL and which already during an operation facilitate a selection of an IOL to be inserted or facilitate an intraoperative selection of the refractive power of an IOL such that, after the implantation of the IOL, the desired target refraction of the eye after surgery is obtained.

An ophthalmic surgical apparatus according to the invention can, for example, include at least one control device and a user interface which, at least intermittently, has data communication with the control device (that is it may, at least in part, establish such data communication). Preferably, inputs for the control device may be entered and/or information originating from or forwarded by the control device may be output by way of this user interface. Furthermore, the ophthalmic surgical apparatus includes a first measuring device which is suitable and intended (or configured and provided) for determining (or ascertaining) at least one value intraoperatively (that is during the operation on the relevant eye), the value being characteristic for the eye to be treated by surgery.

Moreover, the ophthalmic surgical apparatus includes a second measuring device which is suitable and intended for determining at least one value preoperatively and/or intraoperatively, the value being characteristic for the eye to be treated by surgery.

Preferably, the second measuring device is intended for determining preoperative values; however, it would also be conceivable for only values ascertained intraoperatively to be determined. However, a plurality of different values are preferably determined or ascertained.

Furthermore, the ophthalmic surgical apparatus includes a first computing unit which is suitable and intended, using the value determined intraoperatively and the value determined preoperatively and/or intraoperatively, for ascertaining at least one first output value which is characteristic for at least one intraocular lens to be selected. Furthermore, the user interface preferably includes at least one first output device suitable for outputting the output value or a value derived therefrom. This output device may be, for example, a display unit. However, the latter may also have a separate embodiment or be integrated in another device.

Here, the at least one IOL to be selected, which is ascertained by at least one first output value, preferably represents the ascertained IOL (which, in particular, was ascertained during the operation) which is then inserted into the eye.

Hence, according to an aspect of the invention, an ophthalmic surgical apparatus is proposed, via which the values for the selection of a lens obtained intraoperatively are used. Expressed differently, it is conceivable that only one lens is preselected or a preselection is made prior to the operation, or else that there is no selection of a lens prior to the operation.

Here, measurement values of the eye before the operation (that is preoperative measurement values) are preferably specifically ascertained. Furthermore, measurement values are also ascertained intraoperatively and, subsequently, the measurement values ascertained before the operation and the additional measurement values, in particular ascertained intraoperatively on the aphakic eye, are used for the calculation, for example, as described in more detail below, to insert these into an aphakic eye model. In particular, this eye model may be used here for modelling a refractive power of an IOL to be inserted or, in general, of a lens to be inserted.

However, the measurement values may also be inserted into a pseudo-phakic eye model, with this eye model already containing an IOL or still containing the natural lens. These results of an eye model ascertained thus render it possible to select a suitable IOL such that the desired target refraction after surgery is reliably obtained. As a result, it is possible, for example, for a user, such as a medical practitioner, to select a suitable IOL not prior to the operation but during the operation, specifically, for example, immediately after phacoemulsification and the ascertainment of measurement values. Hence, the IOL is selected intraoperatively and not preoperatively within the scope of the invention. In this way, it is also possible to dispense with the above-described quality control.

The above-described control device may preferably assume various functions or be configured to this end. Thus, this control device may be configured to read preoperative values ascertained by the (second) measuring device (or values ascertained or measured preoperatively). Additionally, it may also be configured to read intraoperative values ascertained by the first measuring device. Here, reference is made to the fact that the first measuring device and the second measuring device may be the same measuring device, but that (preferably) different measuring devices may also be used.

Additionally, the control device may also be configured to prompt the user interface to display a value which is characteristic for the intraocular lens. Additionally, the control device may also be configured to prompt the at least one measuring device, or else both measuring devices, to determine or ascertain intraoperative and/or preoperative values.

Furthermore, the control device is preferably configured to prompt the first computing unit to determine a value which represents a refractive error of the eye. Here, preferably, the preoperative measurement values of the eye may be assigned to a first portion of the aforementioned parameters of the model and the intraoperative values of the eye may be assigned to a second portion of the plurality of parameters of the model.

Furthermore, the control device may be configured to prompt the user interface to depict the value which represents a refractive error.

In a further advantageous embodiment, the user interface has input means for inputting data. Here, it is also conceivable for the control device to be adapted or configured such that it awaits a specific input of a user into the user interface before the first measuring device and/or the second measuring device is prompted to determine the preoperative values and/or the intraoperative values.

In a further advantageous embodiment, the ophthalmic surgical apparatus may also include a removal device for removing a natural lens of the eye.

In a further advantageous embodiment, the preoperative values are selected from a group of values which contains a value representing a surface geometry or thickness of the cornea of the eye, a value representing a distance between a corneal vertex of the eye and a retina of the eye and a value representing a distance between the corneal vertex of the eye and a lens of the eye. Advantageously, a plurality of these values and, particularly preferably, all of these values are ascertained and/or taken into account.

Moreover, it is also possible for these aforementioned values to be measured and/or output by the first measuring device.

Additionally, it would also be possible for the first measuring device also to ascertain a value which represents, or is characteristic for, a distance between a corneal vertex and an intraocular lens and/or a value which is determined at least on the basis of an incision introduced into the cornea of the eye and/or a value which represents centering of an intraocular lens in the eye.

It is also possible for a plurality of these values to be output. The IOL to be inserted may be not only monofocal, but also bifocal or multifocal, or may include a variable refractive power. Such accommodatable IOLs are known from the prior art. See, for example, the thesis by M. Bergemann: "Neues mechatronisches System für die Wiederherstellung der Akkomodationsfähigkeit des menschlichen Auges" (2007, ISBN: 978-3-86644-136-1), pages 20 and 21. However, it is advantageous here if a desired target refraction after surgery is achieved at the upper and lower limit of the variable IOL refractive power so that the variability of the IOL may be used in an ideal manner.

In a further advantageous embodiment, the proposed apparatus also includes an optimization algorithm and/or a module for producing an IOL. As known from the optimization of optical systems with software packages, it is possible by way of such an optimization algorithm to optimize the geometry of an IOL such that the eye model supplies the desired target refraction after surgery as a characteristic value. Subsequently, these geometry data may be forwarded to a module for producing an IOL. By way of example, this may be a 3D printer, or else an apparatus for turning (plastic) lenses.

Furthermore, it would also be possible for a preselection of an IOL already to be made prior to an operation and for further values, such as for example a refractive power of the lens, only to be determined intraoperatively and a selection possibly to be corrected on the basis of these values.

In a further advantageous embodiment, a first measuring device is suitable and intended for determining the first measurement value on an aphakic eye. The method described here has the advantage, in general terms, that errors of a patient-specific eye model may be corrected. By way of example, it is generally not easily possible to determine the topography of the corneal rear side which adjoins the aqueous humor.

Since the above-described apparatus and the above-described method are preferably used to compare the actually measured refraction of an aphakic eye model with the aphakic patient-specific eye model, it is possible to eliminate the influence of inaccurate measurement values, such as the topography of the corneal rear side. In other words, it is proposed to compare measurement results of aphakic eyes and eye models with one another in each case. In this way, it is possible to reliably select a well-suited IOL for a patient eye, even in difficult cases. By way of example, such cases may be eyes which were already treated by surgery, for example eyes treated by Lasik. In this case, the cornea of the patient was modified, as a result of which a preoperative IOL selection is very difficult. However, these corneal modifications may be taken into account using the procedures and apparatuses described here and below.

In a further advantageous embodiment, the apparatus includes a second computing unit which is suitable and intended, using at least the value ascertained or determined intraoperatively and the value ascertained or determined preoperatively (or likewise intraoperatively), for ascertaining at least one second output value which is characteristic for a refractive error (or refraction) of the eye after surgery. In this embodiment, it is proposed that the computing unit predicts a refractive error of the eye, in particular on the basis of a computing model using the values determined by the measurement or else measurement values provided differently. Here, this second computing unit may, for example, contain a computer module for predicting a refraction of the eye after surgery. In particular, the aforementioned values are measured values or measurement values.

This computer module in turn may include a transfer means or interface to transfer model data for describing a patient-specific eye model, and also a computing unit which is suitable for ray evaluation, for example optics software such as for example Code-V or Zemax. The data provided to the computing unit or the model data may include preoperative measurement values and/or intraoperative measurement values as well. Additionally, it is also possible to use values based on these values, for example values obtained by computation from preoperative and/or intraoperative data.

Additionally, it is also possible to use synthetic model data which are, or were, obtained by computation from preoperative and intraoperative data.

By way of example, these values may be a number tuple which describes a geometry of the cornea of the patient eye after surgery, which geometry was preferably also obtained via computational simulation on the basis of a corneal geometry ascertained preoperatively and incisions undertaken intraoperatively.

These model data of a patient-specific eye model in this case advantageously describe the associated state of the patient eye in each case and the calculated characteristics describe the refraction of the eye. Depending on the employed model data, it is therefore possible to ascertain the refraction of a phakic, aphakic or pseudo-phakic eye by way of the associated characteristics, wherein, preferably, boundary conditions such as intraocular pressure (IOP) or else the deformation of the cornea by the eyelid holder may furthermore be taken into account.

The characteristics may be used for the selection of a suitable IOL such that, preferably, the refraction of the patient eye in the state after surgery comes close to the target refraction after surgery.

Preferably, the computing unit calculates the aforementioned values on the basis of an eye model. Here, it is possible to use values determined (that is ascertained) preoperatively and values of the eye determined (that is ascertained) intraoperatively as parameters for this eye model. A refractive error of the eye emerging after surgery may be predicted on the basis of these values. This prediction may already be carried out during the intervention, that is intraoperatively, such that, preferably, appropriate adaptations may be undertaken depending on the ascertained refractive error after surgery.

The values used by the computing unit or in a corresponding method, which values represent, or are characteristic for, properties of the eye, and parameters of the eye model, which represent properties of the eye model, may be scalar values or else tuples which themselves have a plurality of scalar values. By way of example, the value which represents the curvature of the cornea of the eye may be a radius of a sphere which approximates the shape of the cornea of the eye. This value may likewise also be an inverse radius of this sphere. Moreover, particularly in the context of astigmatic refractive errors of the eye, this value may be a tuple of two individual values which represent curvatures along different planes of the cornea. Furthermore, the value which represents the curvature of the cornea may be a tuple with for example a plurality of Zernike coefficients which, in a manner known per se, represent an aspherical form of the cornea up to a predetermined order.

By way of example, the value representing the distance between the corneal vertex of the eye and the eye lens of the eye may be directly measured preoperatively. However, other determination methods would also be possible in addition thereto. By way of example, it would be possible for the distance between the corneal vertex and the retina of the eye to be measured and for the measured value of the distance between the eye lens and the retina to be subtracted from this measured value.

In this way, the tuple made of the value of the distance between the corneal vertex of the eye and the retina (and optionally also the tuple made of the value of the distance between the eye lens and the retina) is also a value representing the distance between the corneal vertex of the eye and the eye lens. Furthermore, the value which represents the distance between the corneal vertex of the eye and the eye lens may be related to the main plane of the eye lens, the vertex of the front lens surface or the vertex of the rear lens surface, or else a different physically present or mathematically imagined element of the lens. Hence, it is possible to determine one of these values, which value is characteristic for the relevant distance in this case.

In a further advantageous embodiment, the second computing unit ascertains the output value on the basis of a model of the eye. This means that a computing model, as illustrated above, is used here, the computing model preferably having or containing a multiplicity of parameters. Here, these may be both preoperative measurement values and intraoperative measurement values; preferably, this relates in any case to patient-specific measurement values. In a further advantageous embodiment, this second computing unit is configured in such a way that it determines the second output value taking into account physical properties of a preselected IOL.

Here, this model preferably has a plurality of parameters. Furthermore, the model is based, in particular, on measurement values ascertained preoperatively and intraoperatively. Furthermore, this is preferably a patient-specific model.

Thus, it would be possible for a specific IOL to be selected in advance, but not yet inserted during the operation.

Subsequently, a correspondingly arising refractive error (or a value characteristic for this) is calculated on the basis of both the physical (and/or optical) properties of this IOL and the measured measurement values. Should this refractive error come very close to a desired refractive error or target refractive error, use may in fact be made of the preselected lens. However, should the refractive error ascertained thus deviate more than desired from a target eyesight or refractive error to be obtained, a new calculation may be made, wherein conclusions may be drawn from the result in respect of how the IOL should be modified.

In a further configuration, it is possible for a measurement of the rear side of the capsular bag to be undertaken in an aphakic state of the eye and for the effective lens position (ELP) to be determined therefrom, the effective lens position describing the position of the implanted IOL in the patient eye (or a future position of an IOL to be implanted). The ELP determined thus is therefore part of the group of intraoperative model data in this case. Additionally, the eye length AL and the corneal topography may also be used as preoperative model data.

Furthermore, data of an aforementioned IOL selected preoperatively, such as for example the refractive index, topography, thickness and haptics thereof, are preferably used as preoperative model data. If only the refractive power of an IOL selected preoperatively is known, it is possible to select the refractive index, the topography and a thickness in such a way that these approximately describe the effect of this IOL. For the following illustration, the assumptions that the patient eye is rotationally symmetric and an ideally fitting rotationally symmetric IOL should be selected are made for the sake of simplicity.

Initially, the computing unit makes available an eye model created intraoperatively, the eye model describing the patient eye after surgery. Table 1 reproduced hereinafter shows model data for such a model. Here, this eye model is preferably created at a time at which the patient eye is aphakic and an IOL has not yet been implanted. The model data contain a curvature of the retina and a thickness of the vitreous humor following the retina and a corresponding refractive index.

Furthermore, data of the capsular bag are specified, such as likewise, once again, a curvature and a thickness. Furthermore, the data of the IOL are specified, that is, in this case, the data of the IOL which, for approximation purposes, is inserted first into the eye model created intraoperatively by calculation.

Finally, the corresponding data of the cornea are still specified. The aforementioned ELP is included in the thickness specifications of the aqueous humor, which belong to lines 3 and 5 of Table 1. A result may now be output on the basis of these data, the result describing whether a lens was accordingly selected correctly. Furthermore, it would also be possible to appropriately depict a lens section of an eye or an eye model with an IOL in accordance with the data used in the intraoperative eye model. This is explained hereinafter with reference to the figures.

Therefore, the second computing unit preferably ascertains the second output value on the basis of a model of the eye. Preferably, the second computing unit ascertains the second output value taking into account physical properties of a preselected IOL. This means that these physical data or parameters of a preselected IOL, which for example is used for a first approximation, are included in the model or taken into account by the second computing unit.

In a further advantageous embodiment, the apparatus has a comparison device which compares the second output value with a further value or intended value. By way of example, this intended value may be a desired target refraction or a desired target refractive error of the eye. The comparison device compares the output value ascertained by calculation (which, in particular, likewise represents a refraction) with this intended value and whether the originally selected lens is suitable for the operation may be determined on the basis of this comparison.

By way of example, if the ascertained output values in comparison with the intended value lie within a specific range or within specific limit values (in this case, it is possible, for example, to form a difference of these values or a ratio), the originally selected lens may be considered to be suitable and may be inserted accordingly. If there are deviations going therebeyond, these deviations may be used to determine the direction in which modifications need to be undertaken, for example whether use should be made of a lens with a higher or lower refractive power. Here, it would be possible for other values to be maintained in respect of this further lens and for, for example, only a refractive power to be adapted. Here, these steps can be carried out a number of times, in particular until a suitable selection of an IOL was made.

In a further advantageous embodiment, the first computing unit or the second computing unit ascertains the characteristic value using a beam path prediction device. By way of example, the computing unit which ascertains the refraction after surgery may, as mentioned above, use a beam path prediction device such as for example a ray tracing method. Here, for example, use may be made of suitable software such as Code V or Zemax. Via ray tracing, it is possible to calculate the aberrations of the eye model intraoperatively as well and, in particular, also prior to the implantation of an IOL and, for example, to predict characteristics such as sphere, axis and cylinder. However, other characteristics such as for example Zernike coefficients of the eye model could additionally also be determined.

In general, the model of the eye may be realized in multifaceted ways. By way of example, the model of the eye may be simulated on a computer with the aid of optics software. Examples of such optics software are, as mentioned above, Code V or Zemax. Usually, parameter sets are fed to such software in a suitable format, the parameter sets defining the optical properties of the simulated object, that is of the eye.

In particular, these parameters also include parameters which represent the distances from interfaces, the refractive indices of the media present between the interfaces and the curvatures of the interfaces. A multiplicity of such models have already been developed for the human eye, such as, for example, the Gullstrand eye model.

In particular, the form of the cornea may also be calculated in such an eye model, wherein a finite element model may be resorted to in this case. Here, this calculation may take place before the latter is included in the eye model or else the calculation of the form of the cornea may be an intrinsic component of the eye model. The preferred use of such finite element models renders it possible also to take into account incisions into the cornea which serve for introduction of operating tools into the eye, for the insertion of the intraocular lens or for the correction of refractive errors.

Hence, both values determined (that is ascertained) preoperatively and values determined (that is ascertained) intraoperatively are preferably assigned to the parameters of the eye model in order to determine the refractive error of the eye after surgery by carrying out calculations on the eye model. In a preferred embodiment, the values of the eye determined (that is ascertained) intraoperatively also include a value which may be obtained by a wavefront measurement on the eye. The refractive error of the eye may be deduced directly during the operation on the basis of such a value or else this value may be used to check the consistency of an already used eye model. Optionally, it would also be conceivable to modify specific parameters of the model depending on values, for example the values determined by the wavefront measurement. The wavefront measurement is preferably carried out before the intraocular lens is inserted.

However, it would also be possible to carry out calculations after the insertion of the IOL, possibly in a supplementary manner.

When inserting an intraocular lens with an astigmatic effect, it is particularly advantageous if values of the eye determined (that is ascertained) intraoperatively also include those values which were obtained by a wavefront measurement on the eye since a value obtained thus renders it possible to deduce whether or not the orientation of the inserted intraocular lens should be modified.

The actual insertion of the intraocular lens still includes further method steps, such as, for example, attaching an eyelid holder to the eye, to be precise, in particular, prior to inserting the intraocular lens into the eye, and removing this eyelid holder, to be precise, in particular, after correcting a position or the orientation of the inserted intraocular lens. The eyelid holder is applied to the eye in order to keep the latter open during the intervention. However, this eyelid holder exerts a certain amount of pressure onto the cornea, and so the latter may be deformed by the pressure from the eyelid holder. A cornea deformed thus may lead to wavefront measurements on the eye identifying an apparent refractive error, which may lead to unnecessary changes in the intervention planning.

In a preferred procedure, such problems, which may be traced back to the deformation of the cornea by the eyelid holder, may be avoided by virtue of use being made of a value of the curvature of the cornea determined or ascertained preoperatively as a parameter in the eye model used to determine the refractive error of the eye after surgery.

In a further advantageous embodiment, the first measuring device is a measuring machine selected from a group of measuring machines containing machines for measuring refraction, keratometers for measuring topography, machines for measuring the position of incisions, machines for (in particular contactless) measurement of an intraocular pressure (IOP), machines for measuring layer boundaries (for example an OCT), an analogue or digital ophthalmological operating microscope, an apparatus for measuring distances between eye structures, combinations thereof or the like. Advantageously, the first measuring device may also include a plurality of these measuring machines.

In a further advantageous embodiment, a measuring machine which determines a value characterizing the curvature of the cornea of the eye is a keratoscope or an OCT measuring machine.

In a further advantageous embodiment, a measuring machine for determining the value representing the distance between the corneal vertex of the eye and the retina of the eye is an OCT measuring machine, an ultrasonic measuring machine or a layer boundary measuring machine.

In a further advantageous embodiment, the measuring machine which determines a value representing the distance between the corneal vertex of the eye and the eye lens and/or a machine which determines a value representing the distance between the corneal vertex of the eye and an intraocular lens is an OCT measuring machine or a layer boundary measuring machine.

In a further advantageous embodiment, a measuring machine which determines a value representing centering of the intraocular lens in the eye is a wavefront measuring machine or an ametropia measuring machine.

In a further advantageous embodiment, the model of the eye takes account of at least one parameter which represents a position and, in particular, an orientation and/or length of at least one incision in the cornea of the eye. In particular, such an incision may be undertaken prior to the insertion of the IOL.

Preferably, the model also takes account of a parameter which represents the position and, in particular, the orientation and/or the length of the at least one incision into the cornea of the eye. A value determined on the basis of the at least one incision introduced in the cornea of the eye may be assigned to this parameter.

In a further advantageous embodiment, the aforementioned output value is characteristic for a refractive power of the intraocular lens to be selected. Here it is possible, as mentioned above, for other data or parameters of the intraocular lens to be selected to be maintained and for merely a refractive power to be adapted. Thus, for example, the computing device may be configured to determine the value representing the intraocular lens with the aid of the Haigis formula, the Hoffer formula, the Holladay formula or the SRK/T formula or a different calculation procedure.

In this case, the value characterizing the intraocular lens may, for example, be the refractive index or a material designation of the material used for the lens of the intraocular lens. Additionally, this may also relate to a radius of curvature of one of the two surfaces, or else of both surfaces, of the intraocular lens, or else this may relate to a designation for a type of the intraocular lens to be used, under which the relevant intraocular lens is commercially available.

Furthermore, the present invention is also directed to a selection method for selecting lenses and, in particular, intraocular lenses. Here, at least one first value which is characteristic for an eye to be treated by surgery is provided. Furthermore, at least one second value which is characteristic for an aphakic eye to be equipped with an intraocular lens to be selected is provided. Furthermore, at least the first value and the second value and/or values derived therefrom are input into a computing unit and at least one output value is ascertained, the output value being characteristic for an intraocular lens to be selected. The values may be measurement values; however, it would also be conceivable to use calculated values.

Preferably, the first value and the second value are values which are characteristic for the same patient and, in particular, for the same eye of the same patient. Reference is made to the fact that the manner in which the respective (measurement) values are obtained, for example by measurement or simulation or the like, is nonessential for the present method. Nor is it necessary for these values to be obtained by a treating medical practitioner. For a method according to the invention it is also once again decisive that a selection of the IOL is made on the basis of these values.

In a preferred embodiment, at least one output value is ascertained on the basis of the first value and the second value, the ascertained output value being characteristic for a refractive error of an eye equipped with a predetermined lens. Preferably, at least one value, in particular the first value, is a value describing an aphakic eye.

In a further advantageous embodiment, the output value is compared to a value which is characteristic for a preselected IOL. Preferably, a decision is made on the basis of this comparison as to whether the preselected IOL is final and, in particular, may be used for an operation which is already underway or for a future operation.

In a further preferred embodiment, the currently available types of IOL may be known to the ophthalmic surgical apparatus and, for example, be stored in a database which may be accessed by the control device and/or the first computing device.

In order to ascertain preoperative values, it is possible for measurements to be carried out on the eye prior to the intervention with the second measuring device. These preoperative values each represent properties of the eye prior to the intervention.

Furthermore, a multiplicity of values may preferably be generated by measurements. Here, this may be, in particular, a value representing the curvature of the cornea, a value representing the distance between the corneal vertex and the lens of the eye and a value representing a distance between the corneal vertex and the retina of the eye.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
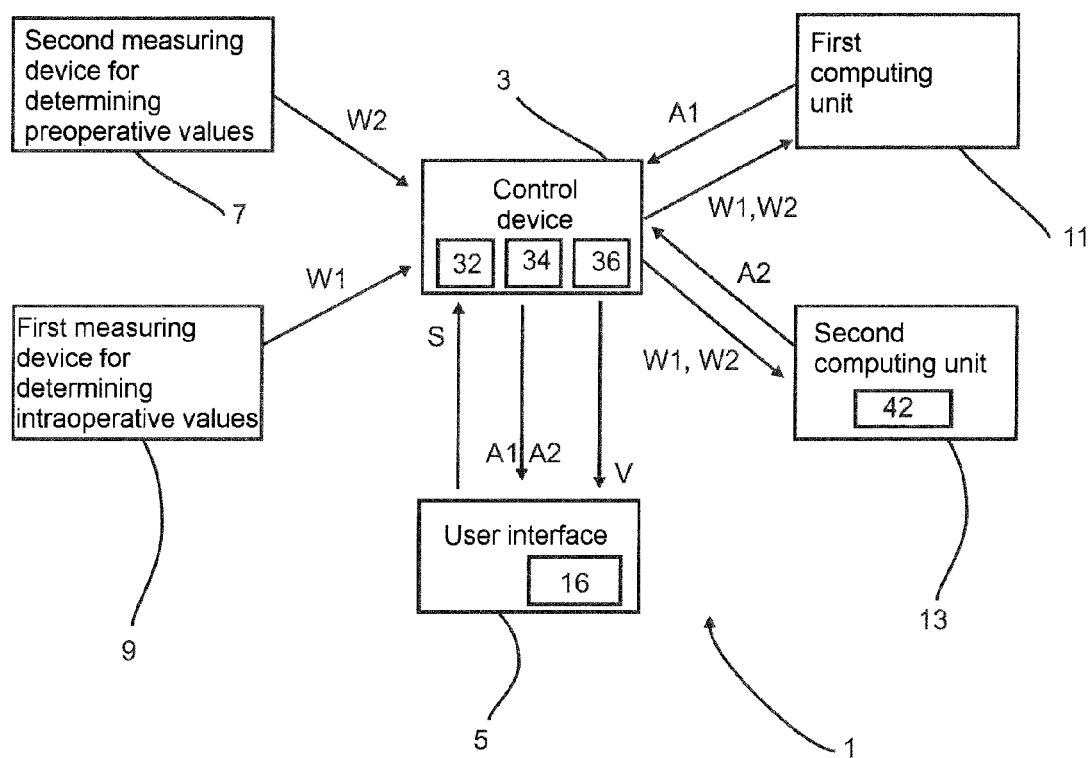
FIG. 1 is a schematic illustration of an ophthalmic surgical apparatus according to the present invention.

FIG. 1 shows a schematic illustration of an ophthalmic surgical apparatus 1 according to the invention. With the aid of this ophthalmic surgical apparatus 1, it is possible to carry out a further method, explained in the figures, for inserting an intraocular lens into an eye. To this end, the ophthalmic surgical apparatus 1 includes a control device 3 and a user interface 5. This user interface 5 may communicate with the control device 3 and/or interchange signals or data with the latter. Furthermore, the apparatus includes a first measuring device 9 for determining intraoperative values W1 of an eye (or values of an eye to be ascertained intraoperatively) and a second measuring device 7 for determining preoperative and/or intraoperative values W2 of an eye (that is, values of an eye to be ascertained preoperatively and/or intraoperatively). Additionally, provision is made of a first computing unit 11 for selecting an intraocular lens and a second computing unit 13 for determining a refractive error after surgery. Reference sign 16 denotes a display device for displaying values, for example an output value which is characteristic for an IOL to be selected.

Here, it would be possible for the apparatus shown in FIG. 1 to be constructed as a distributed system, for example by virtue of the first measuring device and the second measuring device being separate devices which are provided at different locations and/or which are used at different times and, when necessary, by different operators as well, in particular in order to carry out the measurements on the eye of a patient. The measurement values W1 captured by the first measuring device 9 and the measurement values W2 captured by the second measuring device 7 are transferred to the control device 3 as measurement data. The control device 3 forwards the measurement values, or data or values derived therefrom, to the two computing units 11, 13.

Advantageously, the control device 3 has a memory device 32 which is suitable and intended for storing these measurement values or data derived from these measurement values. However, this memory device 32 may also be present in the respective measuring devices or a memory device may additionally also be present. Also, as depicted schematically in FIG. 1, the control device 3 may be embodied as a distributed system and, at least in part, be integrated in the individual measuring devices 7 and 9.

By way of example, the user interface 5 may include a display device such as a screen 16, which is suitable for displaying and outputting data. Additionally, the user interface 5 may include an input device such as a keyboard or mouse, via which the user may input data. Furthermore, it is also possible for the user interface 5 to be constructed as a distributed system. Thus, some of the functionality may be integrated into the respective measuring devices 7 and 9 and/or further parts may also be integrated in further system components not depicted here. In particular, the screen 16 may also be a micro-display, the image information of which may be mirrored into eyepieces of an optical observation system.

Reference sign 11 denotes a first computing unit which is provided for ascertaining an intraocular lens to be selected. Here, this first computing unit is preferably realized as a software module which is implemented in one or more computers. However, further software may also be provided in these computers in this case, the software providing functions of the control device 3, the user interface 5 and the two measuring devices 7, 9. This first computing unit 11 may ascertain, and/or output to the control device 3, a first output value A1 which is characteristic for an IOL to be selected. Preferably, this is a value which uniquely characterizes this IOL, for example an ID number or else specific physical properties which are characteristic for this IOL. This first output value A1 may also be output from the control device 3 to the user interface 5 and it may also be displayed by the display device 16.

The second computing unit 13 may also be embodied as a software module. Here, this second computing unit 13 takes account of at least the measurement values from the first measuring device 9 and from the second measuring device 7. However, it would also be possible for measurements only to be undertaken on an aphakic eye under certain circumstances and for all relevant data to be obtained from these measurement values. The second computing unit 13 may output a second output value A2 which is characteristic for the refractive error of the eye. Here, this second output value A2 may also be transferred to the control device 3 and may also be output to the user interface 5 (in particular by the control device 3) and/or displayed by the display device 16.

Reference sign 34 denotes a comparison device which compares the output value A2 which is output by the second computing unit 13 and is characteristic for a refractive error of the eye using the preselected IOL to an intended value S or to a target refraction. Preferably, this intended value S may be input by way of the user interface 5.

Reference sign 36 denotes a calculation unit which outputs a value V characteristic for this comparison, such as, for example, a difference or ratio of the values compared to one another. Reference sign 42 denotes a beam path prediction device such as a ray tracing module.

Figure 2:
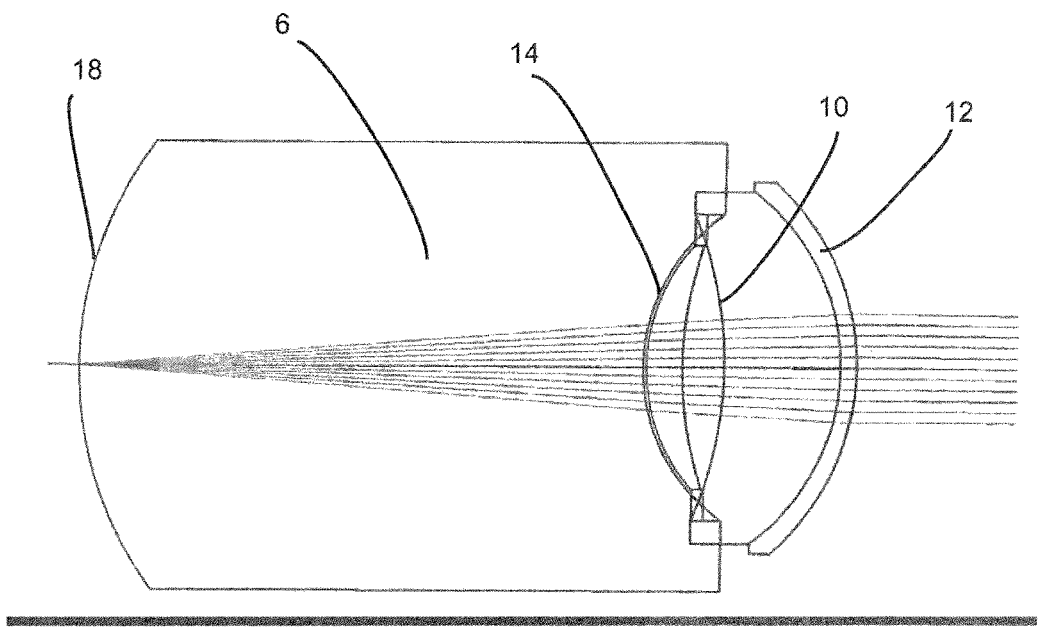
FIG. 2 shows an illustration of a calculated eye model.
Figure 3:
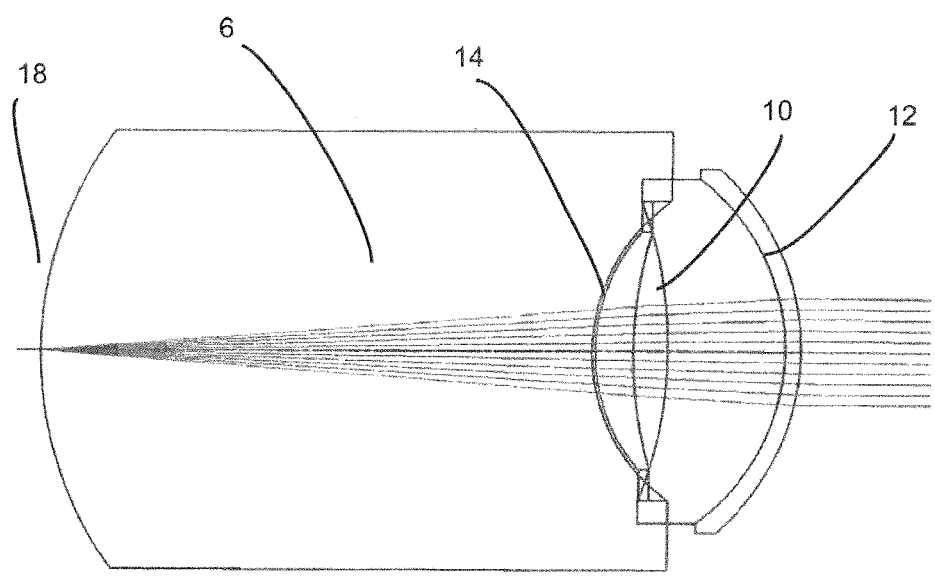
FIG. 3 shows an illustration of a modified calculated eye model.

FIGS. 2 and 3 serve to explain an apparatus according to the invention and a method according to the invention. As already mentioned above, an object of the invention includes providing an apparatus and a method, via which a correct lens may be selected intraoperatively. In accordance with an example elucidated by FIGS. 3 and 4, a patient eye is selected, for which a target refraction of −1 diopter myopia after surgery was agreed with the patient such that the patient has ideal visual comfort without spectacles at a distance of 1 meter. A biconvex symmetric IOL with a curvature $\rho=1/12.1$ mm$=0.082645$/mm and a thickness of 1.3 mm and a refractive index of 1.464 was selected preoperatively for this patient in a preliminary examination.

A measurement of the rear side of the capsular bag is undertaken in the aphakic state and the effective lens position (ELP) is determined therefrom together with other data. FIG. 3 now shows a lens section which was generated via the data record contained in Table 1. Here, reference sign 12 relates to the cornea, reference sign 10 relates to the IOL and reference sign 14 relates to the capsular bag. Aqueous humor is situated between the lens 10 and the cornea and, likewise, between the IOL and the capsular bag 14. Reference sign 6 denotes the vitreous humor of the eye and reference sign 18 denotes the retina. This data record of the aforementioned data may be transferred into a computer module for predicting the refraction after surgery such that characteristics for evaluating the refractive error of the eye model may be determined, this simultaneously representing a prediction of the refractive error of the eye after surgery if the corresponding IOL were to be implanted.

Table 1 below shows the data record for describing the eye model in this embodiment.

TABLE 1

Data record for describing the eye model shown in FIG. 3 with a preselected IOL

|   | Curvature ρ [1/mm]] | Thickness [mm] | Refractive index n (λ = 550 nm) |
|---|---|---|---|
| 1 (Retina) | +0.086207 | 17.72 | 1.336 |
| 2 (Capsular bag-rear side) | +0.170648 | 0.1 | 1.386 |
| 3 (Capsular bag-front side) | +0.173611 | 1.115 | 1.336 |
| 4 (IOL-rear side) | +0.082645 | 1.3 | 1.464 |
| 5 (IOL-front side) | −0.082645 | 3.65 | 1.336 |
| 6 (Cornea-rear side) | −0.147059 | 0.5 | 1.376 |
| 7 (Cornea-front side) | −0.129870 | | |

If, in general, the prediction of the refractive error lies close enough to the target refraction after surgery or the intended value (for example if the difference between the predicted refractive error and the target refraction after surgery in terms of magnitude is less than 1 diopter, preferably less than 0.4 diopter and particularly preferably less than 0.2 diopter), then the IOL selected intraoperatively is identical to the IOL selected preoperatively and the process of intraoperative IOL selection is completed. In this case, the IOL selected preoperatively, which does not deviate, or only deviates slightly, from the ascertained IOL, may be inserted.

If the magnitude of the aforementioned difference has a distance from the desired target refraction after surgery which is too large, an IOL type with different parameters, better suited thereto, is selected. From the sign of this difference, it is possible to deduce whether an IOL with a higher or lower refractive index is selected for the next iteration. Subsequently, the model data from Table 1 are modified in accordance with the newly selected IOL in such a way that they describe the newly selected IOL and the position thereof in the patient eye.

Subsequently, the associated refractive error characteristics are determined from the model data, as well as the difference between the predicted refractive error and the target refraction after surgery. In the next step, a decision is made as to whether the magnitude of this difference is sufficiently small or whether a further, iteration needs to take place.

What would emerge from the illustration in FIG. 2 and the data record listed in Table 1 is that the depicted rays coincide at a distance of approximately 40 cm from the cornea (to the right) and would therefore form ideal eyesight in this region. However, as mentioned above, the ideal eyesight should lie in the region of 1 meter. In other words, a myopic refractive error of −2.46 diopters emerges, for example, as a characteristic in the IOL selected preoperatively in the case of the model data from Table 1. Therefore, the refractive error of 2.46 diopters predicted for the eye after surgery deviates by 1.46 from the target refraction after surgery of −1 diopter, and so an improved target refraction after surgery is obtained if an IOL with a lower refractive power is implanted.

By way of the interaction between the computing units 11 and 13 of an apparatus according to the invention, an IOL is now selected from the available IOLs, in which the associated generated patient-specific eye model supplies a value as a characteristic for the refractive error which lies sufficiently closely to the desired target refraction after surgery. In this embodiment, this IOL selected intraoperatively is described by the following specifications: biconvex, curvature ρ=1/13.3 mm=0.075188 mm, thickness 1.1 mm and refractive power n=1.464. Table 2 below shows the corresponding model data.

TABLE 2

Data record for describing the eye model shown in FIG. 3 with the second IOL

|   | Curvature ρ [1/mm]] | Thickness [mm] | Refractive index n (λ = 550 nm) |
|---|---|---|---|
| 1 (Retina) | +0.086207 | 17.72 | 1.336 |
| 2 (Capsular bag-rear side) | +0.170648 | 0.1 | 1.386 |
| 3 (Capsular bag-front side) | +0.173611 | 1.215 | 1.336 |
| 4 (IOL-rear side) | +0.075188 | 1.1 | 1.464 |
| 5 (IOL-front side) | −0.075199 | 3.75 | 1.336 |
| 6 (Cornea-rear side) | −0.147059 | 0.5 | 1.376 |
| 7 (Cornea-front side) | −0.129870 | | |

FIG. 3 shows an associated sectional image. A value of −1.11 diopters is determined by calculation as the characteristic for the refractive error, and so there is only a small deviation from the target refraction after surgery of −1 diopter. By way of the user interface 5, it is now communicated to the user or surgeon that the desired target refraction after surgery is achieved for the patient if this IOL is used. In the image from FIG. 4, the rays would, to the right, coincide at approximately a distance of one meter from the cornea, corresponding to the desired specifications. It is possible to see that the selected IOLs, shown in FIGS. 2 and 3, differ from one another.

Figure 4:
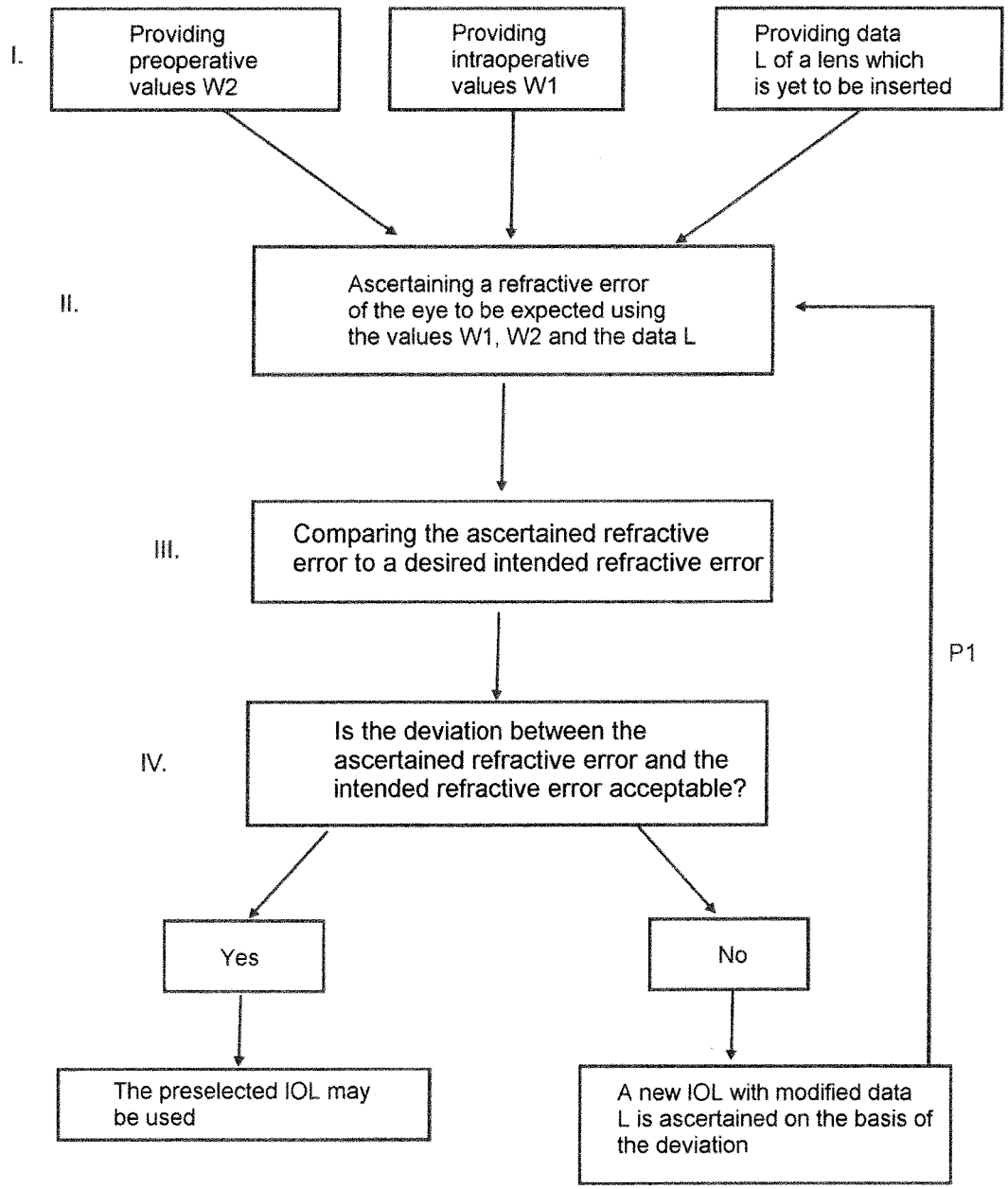
FIG. 4 shows an illustration of a sequence or the procedure when ascertaining an IOL in accordance with a first embodiment; and, FIG. 5 shows an illustration of a corresponding sequence or the procedure when ascertaining an IOL in accordance with a further embodiment.

FIG. 4 shows a method which may be carried out via an apparatus according to the invention in accordance with a first variant. Accordingly, preoperative and intraoperative measurement values are initially made available. Here, these may be ascertained by measurements; however, other options for ascertaining these data would also be conceivable. These data may also be predetermined by a medical practitioner; however, it would also be possible for these values to be ascertained merely by the use of instruments or machines and, in this respect, there is no need for the involvement of a medical practitioner.

In this first variant of the method, preoperative measurement values W2 and intraoperative measurement values W1, and also data L of a lens which has not yet been inserted, are provided in a method step I. These data are initial data which are used for a calculation. However, it is also possible to adopt data, for example, from a transparent film in this case.

A refractive error of the eye to be expected is determined in a method step II using the measurement values W1 and W2 and the data L. Here, the measured values are, once again, for example the preoperative values such as the curvature of the cornea or else the distance from the corneal vertex to the retina. The refractive error now ascertained is compared to a desired intended refractive error (method step III). In a further method step IV, a deviation between an ascertained refractive error and the intended refractive error is ascertained and a check is carried out as to whether this deviation is acceptable.

By way of example, a decision could be made that this deviation is acceptable if there is only a deviation in a region of 0.2 diopter or less. In this case, use can be made of the preselected IOL. If the deviation between the ascertained refractive error and the intended refractive error (method step IV) is unacceptable, a new IOL with modified data L may be ascertained on the basis of the deviation.

The modified data L of this IOL are once again used in method step II, as indicated by the arrow P1, in order (in place of the initial data for the preselected IOL) to ascertain the refractive error in a further run through of method steps II and III. In accordance with method step IV, there once again is a query as to whether the deviation between the ascertained refractive error and the intended refractive error is acceptable. These method steps I to IV are repeated until, finally, the deviation is acceptable and the lens ascertained in this case may be used for the operation. Hence, the method shown here is based on an iteration of an examination by calculation as to whether a preselected IOL is suitable for use. Reference is made to the fact that these steps do not require measurements on the eye of the patient to be carried out. Thus, while the aforementioned values W1 and W2 are determined by measurements in particular, preferably no further measurements are carried out any longer within the scope of the steps or iterations described here; instead, a desired result, for example a desired refraction, is approached in a predetermined number of steps.

In FIG. 4, the assumption was made that the employed lenses are rotationally symmetric lenses. If the preoperative corneal geometry exhibits a deviation from rotational symmetry, it is also possible to form a toric IOL preoperatively. In this case, the employed coordinate system is oriented in an additional step in such a way that the Z-axis corresponds to an optical axis of the eye and that the main curvatures of the cornea are accommodated in the XZ-plane and in the YZ-plane. In this case, too, the model data may be described in a similar fashion to the aforementioned tables. However, the curvatures in this case additionally deviate from one another in the X-direction and Y-direction. In this case, it is likewise advantageous if the correct orientation of the IOL in the patient eye is taken into account in the model data, on which in turn the calculations with the characteristic are based. In these cases, it would be possible to complement the aforementioned table with model data.

Additionally, it would also be possible to use synthetic model data, that is model data which are not directly measured, for example the topography obtained if the deformation of the corneal topography by the undertaken incisions is taken into account could be used as the corneal topography of the eye model. Here, it is also possible for these incisions to be placed deliberately in such a way that deviations of the corneal topography from the rotational symmetry are reduced. Here, this procedure is referred to as limbal relaxing incision (LRI).

Additionally, it would also be possible to use synthetic model data which predict the corneal topography of the eye model after healing, in particular in the state after surgery.

Figure 5:
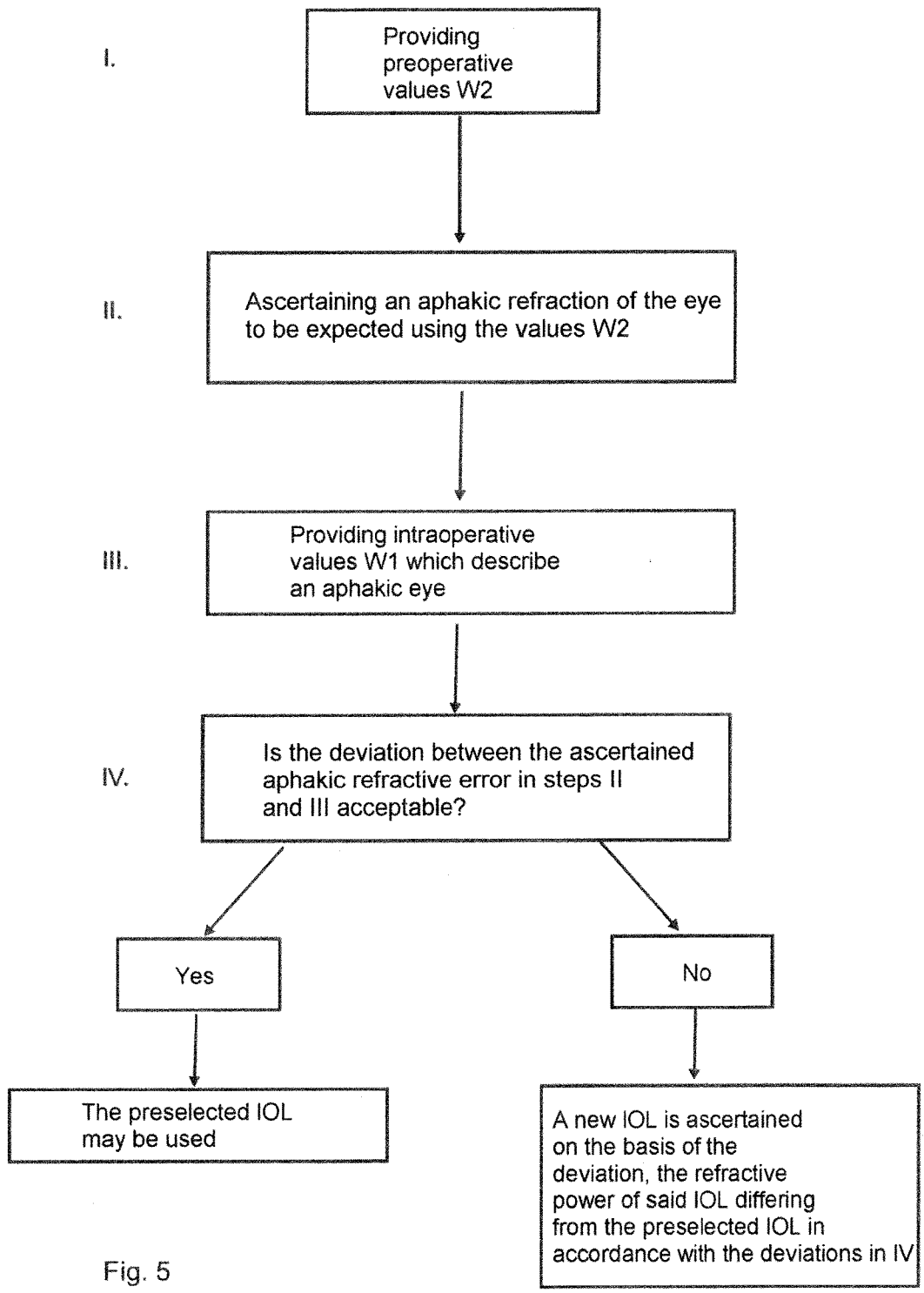

Finally, FIG. 5 shows a further sequence of a method by means of an apparatus according to the invention. Preoperative values W2 are provided in this method (method step I). The example now shown describes a method, with the aid of which the refraction of the patient after surgery lies closer to the target refraction after surgery.

The preoperative data may be a corneal topography, an eye length, a corneal thickness, et cetera. Using this, there is a preoperative IOL selection, wherein in particular a patient-specific eye model may be used to this end, as described above with reference to FIG. 1 (method step II). However, an expected aphakic refraction of the eye is now determined using these (measurement) values. In other words, the aphakic refraction is predicted using an aphakic patient-specific eye model.

In a further method step, intraoperative (measurement) values W1 describing an aphakic eye are provided (method step III). Here, there may be an intraoperative aphakic refraction measurement. In this case, it is preferably possible to correct interfering effects, such as for example a pressure of the eyelid holder on the cornea or influences of the intraocular pressure.

Like in the variant described above, a deviation between the ascertained aphakic refractive error in the aforementioned steps II and III is once again determined here, and there is a determination as to whether these deviations are acceptable. The selected IOL may be used if the deviations are acceptable. If the results are unacceptable, a new IOL may once again be ascertained on the basis of the deviation, wherein the refractive power thereof differs from the preselected IOL in accordance with the theoretical deviations from method step IV. Preferably, there is a new selection of an IOL, wherein, particularly preferably, there is only variation in a refractive index.

Reference is once again made to the fact that, initially, no lens is inserted in this method. The lens may only be used or inserted if it corresponds to the specifications after a certain number of iterations.

It is understood that the foregoing description is that of the preferred embodiments of the invention and that various changes and modifications may be made thereto without departing from the spirit and scope of the invention as defined in the appended claims.

LIST OF REFERENCE SIGNS

1 Ophthalmic surgical apparatus
3 Control device
5 User interface
6 Vitreous humor
7 Second measuring device
9 First measuring device
10 Intraocular lens
11 First computing unit
12 Cornea
13 Second computing unit
14 Capsular bag
16 Display device
18 Retina
32 Memory device
34 Comparison device
36 Calculation unit
42 Beam path prediction device
W1, W2 (Measurement) values
A1, A2 Output values
S Intended value, target refraction
V Value for the comparison
L Data for a preselected IOL which, however, has not yet been inserted

What is claimed is:
1. An ophthalmic surgical apparatus comprising:
a control device;
a user interface configured to, at least intermittently, be in data communication with said control device;
a first measuring device configured to ascertain at least one first value (W1) intraoperatively;

said first value (W1) being characteristic for an eye to be treated by surgery;

a second measuring device configured to determine at least one second value (W2) which is determined at least one of preoperatively and intraoperatively;

said second value (W2) being characteristic for the eye to be treated by surgery;

a first computing unit configured to use said first value (W1) and said second value (W2) in ascertaining at least one first output value (Al) which is characteristic for at least one intraocular lens to be selected, wherein the selected intraocular lens is to be inserted into the eye, and wherein a replacement of the inserted intraocular lens during surgery is dispensed with; and, a second computing unit configured to determine on the basis of a model of the eye at least a second output value (A2), which is characteristic of a postoperative refractive error of the eye, using the intraoperatively determined first value (W1) and said second value (W2) determined preoperatively.

2. An ophthalmic surgical apparatus comprising:

a control device;

a user interface configured to, at least intermittently, be in data communication with said control device;

a first measuring device configured to ascertain at least one first value (W1) intraoperatively;

said first value (W1) being characteristic for an eye to be treated by surgery;

a second measuring device configured to determine at least one second value (W2) which is determined at least one of preoperatively and intraoperatively;

said second value (W2) being characteristic for the eye to be treated by surgery;

a first computing unit configured to use said first value (W1) determined intraoperatively and said second value (W2), determined at least one of preoperatively and intraoperatively, for ascertaining at least one first output value (A1) which is characteristic for at least one intraocular lens to be selected, wherein the selected intraocular lens is to be inserted into the eye, and wherein a replacement of the inserted intraocular lens during surgery is dispensed with; and, a second computing unit configured to determine at least one second output value (A2), which is characteristic of a postoperative refractive error of the eye, using said first value (W1) determined intraoperatively and said second value (W2) determined preoperatively, wherein said second computing unit is configured to determine said second output value (A2) considering physical properties of a preselected intraocular lens.

3. The ophthalmic surgical apparatus of claim 1, wherein said first measuring device is configured to determine said first value (W1) at an aphakic eye.

4. The ophthalmic surgical apparatus of claim 2, wherein said first measuring device is configured to determine said first value (W1) at an aphakic eye.

5. The ophthalmic surgical apparatus of claim 2, wherein said second computing unit is configured to ascertain said second output value (A2) on the basis of a model of the eye.

6. The ophthalmic surgical apparatus of claim 2, wherein said second computing unit is configured to determine said second output value (A2) taking into account physical properties of a preselected intraocular lens.

7. The ophthalmic surgical apparatus of claim 1, wherein said ophthalmic surgical apparatus includes a comparison device configured to compare said second output value (A2) with an intended value.

8. The ophthalmic surgical apparatus of claim 2, wherein said ophthalmic surgical apparatus includes a comparison device configured to compare said second output value (A2) with an intended value.

9. The ophthalmic surgical apparatus of claim 1, wherein said first computing unit is configured to ascertain said at least one first output value (A1) using a beam path prediction device.

10. The ophthalmic surgical apparatus of claim 2, wherein said first computing unit is configured to ascertain said at least one first output value (A1) using a beam path prediction device.

11. The ophthalmic surgical apparatus of claim 1, wherein at least one of said first measuring device and said second measuring device includes at least one measuring machine selected from a group of measuring machines which includes machines for measuring refraction, keratometers for measuring topography, machines for measuring the position of incisions, machines for contactless measurement of an intraocular pressure, machines for measuring layer boundaries, an ophthalmological operating microscope, and combinations thereof.

12. The ophthalmic surgical apparatus of claim 2, wherein at least one of said first measuring device and said second measuring device includes at least one measuring machine selected from a group of measuring machines which includes machines for measuring refraction, keratometers for measuring topography, machines for measuring the position of incisions, machines for contactless measurement of an intraocular pressure, machines for measuring layer boundaries, an ophthalmological operating microscope, and combinations thereof.

13. The ophthalmic surgical apparatus of claim 1, wherein said model of the eye takes account of at least one parameter which represents at least one of a position, an orientation and a length of at least one incision in the cornea of the eye.

14. The ophthalmic surgical apparatus of claim 1, wherein said model of the eye takes account of at least one parameter which represents centering of the intraocular lens in the eye.

15. The ophthalmic surgical apparatus of claim 1, wherein said first output value (A1) is characteristic for a refractive power of the intraocular lens to be selected.

16. The ophthalmic surgical apparatus of claim 2, wherein said first output value (A1) is characteristic for a refractive power of the intraocular lens to be selected.

17. The ophthalmic surgical apparatus of claim 1, wherein said control device is configured such that it awaits a predetermined input of the user into said user interface before at least one of said first and said second measuring device is prompted to determine intraoperative and/or preoperative measurement values.

18. The ophthalmic surgical apparatus of claim 2, wherein said control device is configured such that it awaits a predetermined input of the user into said user interface before at least one of said first and said second measuring device is prompted to determine intraoperative and/or preoperative measurement values.

19. The ophthalmic surgical apparatus of claim 1, wherein said user interface includes at least one output device configured to output said first output value (A1) or a value derived therefrom.

20. The ophthalmic surgical apparatus of claim 2, wherein said user interface includes at least one output device suitable for outputting said first output value (A1) or a value derived therefrom.

21. A method for selecting lenses including intraocular lenses, the method comprising the steps of:

providing at least one first value (W1) which is characteristic for an eye to be treated by surgery;

providing at least one second value (W2) which is characteristic for an aphakic eye to be equipped with an intraocular lens to be selected;

inputting at least the first value (W1) and the second value (W2) into a computing unit and ascertaining at least one output value (A1) which is characteristic for an intraocular lens to be selected, wherein the selected intraocular lens is to be inserted into the eye, and wherein a replacement of the inserted intraocular lens during surgery is dispensed with; and, determining at least one third value on the basis of the first value (W1) and the second value (W2), and considering physical properties of a preselected intraocular lens, wherein the third value is characteristic of a refractive error of an eye to be fitted with the preselected intraocular lens.

* * * * *